United States Patent
Fujimoto

(10) Patent No.: US 11,472,841 B2
(45) Date of Patent: Oct. 18, 2022

(54) IMMUNOGENIC COMPOSITION

(71) Applicant: MENICON CO., LTD., Aichi (JP)

(72) Inventor: Miya Fujimoto, Aichi (JP)

(73) Assignee: MENICON CO., LTD., Aichi (JP)

( * ) Notice: Subject to any disclaimer, the term of this patent is extended or adjusted under 35 U.S.C. 154(b) by 139 days.

(21) Appl. No.: 16/961,238

(22) PCT Filed: Jan. 18, 2019

(86) PCT No.: PCT/JP2019/001377
§ 371 (c)(1),
(2) Date: Jul. 9, 2020

(87) PCT Pub. No.: WO2019/142886
PCT Pub. Date: Jul. 25, 2019

(65) Prior Publication Data
US 2021/0061858 A1    Mar. 4, 2021

(30) Foreign Application Priority Data
Jan. 19, 2018    (JP) .............................. JP2018-007152

(51) Int. Cl.
*C07K 7/08*    (2006.01)
*C07K 14/00*    (2006.01)

(52) U.S. Cl.
CPC ............... *C07K 7/08* (2013.01); *C07K 14/00* (2013.01)

(58) Field of Classification Search
None
See application file for complete search history.

(56) References Cited

U.S. PATENT DOCUMENTS

| | | | |
|---|---|---|---|
| 2012/0058066 A1* | 3/2012 | Nagai | A61L 31/145 424/70.1 |
| 2012/0282292 A1 | 11/2012 | Collier et al. | |
| 2014/0086952 A1 | 3/2014 | Sun et al. | |

FOREIGN PATENT DOCUMENTS

| | | |
|---|---|---|
| JP | 2014512385 | 5/2014 |
| JP | 2015124212 | 7/2015 |
| WO | 2007000979 | 1/2007 |
| WO | 2010103887 | 9/2010 |
| WO | 2012145355 | 10/2012 |
| WO | 2016004213 | 1/2016 |
| WO | 2017098627 | 6/2017 |

OTHER PUBLICATIONS

Zhang et al. Rational design of charged peptides that self-assemble into robust nanofibers as immune-functional scaffolds. Acta Biomaterialia 55 (2017) 183-193.*
Yang et al. Single Dose of Protein Vaccine with Peptide Nanofibers as Adjuvants Elicits Long-Lasting Antibody Titer. ACS Biomater Sci Eng. Jun. 11, 2018;4(6):2000-2006. Epub Sep. 15, 2017.*
Jai S Rudra et al., "A self-assembling peptide acting as an immune adjuvant," Proc Natl Acad Sci, vol. 107, Jan. 2010, pp. 622-627.
P. Chen et al., "Self-assembly of ionic-complementary peptides: a physicochemical viewpoint," Colloids and Surfaces A: Physicochemical and Engineering Aspects, vol. 261, Jul. 2005, pp. 3-24.
"Search Report of Europe Counterpart Application", dated Oct. 18, 2021, p. 1-p. 10.
"International Search Report (Form PCT/ISA/210) of PCT/JP2019/001377," dated Mar. 12, 2019, with English translation thereof, pp. 1-4.
Brian M. Friedrich, et al., "Supramolecular peptide hydrogel adjuvanted subunit vaccine elicits protective antibody responses against West Nile virus," Vaccine, Sep. 2016 , pp. 1-4.

* cited by examiner

*Primary Examiner* — Nianxiang Zou
(74) *Attorney, Agent, or Firm* — JCIPRNET

(57) ABSTRACT

Provided is an immunogenic composition which contains a self-assembling peptide as an adjuvant and can increase the immunogenicity of various antigens. The present invention provides an immunogenic composition including: a peptide hydrogel containing a positively or negatively charged self-assembling peptide and an aqueous medium; and an antigen, in which the self-assembling peptide is not covalently bonded to the antigen.

14 Claims, 9 Drawing Sheets
Specification includes a Sequence Listing.

TEST SAMPLE 1

TEST SAMPLE 2

TEST SAMPLE 3

TEST SAMPLE 4

IMMUNOGENIC COMPOSITION

CROSS-REFERENCE TO RELATED APPLICATION

This application is a 371 application of the International PCT application serial no. PCT/JP2019/001377 filed on Jan. 18, 2019, which claims the priority benefits of Japan Patent Application No. 2018-007152, filed on Jan. 19, 2018. The entirety of each of the above-mentioned patent applications is hereby incorporated by reference herein and made a part of this specification.

TECHNICAL FIELD

The present invention relates to an immunogenic composition containing an antigen and a peptide hydrogel, and a method for producing the immunogenic composition.

BACKGROUND ART

A self-assembling peptide is a peptide that can spontaneously assemble in an aqueous solution through an interaction between peptide molecules to form a nanofiber. The self-assembling peptides are widely used, for example, for a cell culture substrate, a hemostatic material, a bone filling material, a drug delivery substrate, an artificial vitreous body, an ophthalmic surgical auxiliary material, cosmetics, and a pressure ulcer preparation (for example, Patent Literature 1).

In recent years, use of a self-assembling peptide such as RADARADARADARADA (SEQ ID No: 18) as an adjuvant has been proposed (Patent Literature 2 and 3 and Non-Patent Literature 1).

REFERENCE LIST

Patent Literature

Patent Literature 1: WO2010/103887
Patent Literature 2: US2012/0282292A1
Patent Literature 3: Published Japanese Translation No. 2014-512385

Non-Patent Literature

Non-Patent Literature 1: Vaccine, 2016 Nov 4; 34 (46): 5479-5482

SUMMARY

Technical Problem

An object of the present invention is to provide an immunogenic composition which contains a self-assembling peptide as an adjuvant and can increase the immunogenicity of various antigens.

Solution to Problem

According to an aspect of the present invention, there is provided an immunogenic composition including: a peptide hydrogel containing a positively or negatively charged self-assembling peptide and an aqueous medium; and an antigen, in which the self-assembling peptide is not covalently bonded to the antigen.

In one embodiment, the above-described self-assembling peptide has a charge of +3, +2, −3, or −2 per peptide molecule at a physiological pH.

In one embodiment, the above-described self-assembling peptide has a charge of +3 or +2 per peptide molecule at a physiological pH.

In one embodiment, the number of amino acid residues constituting the above-described self-assembling peptide is 10 to 32.

In one embodiment, a concentration of the above-described self-assembling peptide contained in the above-described immunogenic composition is 0.3 w/v % to 2.0 w/v %.

In one embodiment, the above-described self-assembling peptide is a peptide having an amino acid sequence (A) described below.

Amino acid sequence (A): $a_1b_1c_1b_2a_2b_3db_4a_3b_5c_2b_6a_4$, (In the amino acid sequence, $a_1$ to $a_4$ each represent a basic amino acid residue; $b_1$ to $b_6$ each represent a non-charged polar amino acid residue and/or a hydrophobic amino acid residue, provided that at least five thereof each represent a hydrophobic amino acid residue; $c_1$ and $c_2$ each represent an acidic amino acid residue; and d represents a hydrophobic amino acid residue or a non-charged polar amino acid residue.)

In one embodiment, the above-described self-assembling peptide is selected from peptides represented by SEQ ID Nos: 1 to 16.

In one embodiment, the above-described self-assembling peptide is selected from peptides represented by SEQ ID Nos: 1, 15, and 16.

In one embodiment, a molecular weight of the above-described antigen is 6.0 kDa to $1.0 \times 10^3$ kDa.

In one embodiment, the above-described antigen contains a positively charged protein at a physiological pH.

In one embodiment, the above-described antigen includes an antigen derived from food, a mite, house dust, a plant, or an animal.

In one embodiment, the above-described antigen includes an antigen of a mite allergy, an antigen of an egg allergy, or pollen.

In one embodiment, the above-described antigen includes at least one selected from a group consisting of ovalbumin, casein, lysozyme, and papain.

Effects of Invention

According to the immunogenic composition of the present invention, the immunogenicity of various antigens can be increased by appropriately selecting a self-assembling peptide.

DESCRIPTION OF THE EMBODIMENTS

Figure 1:
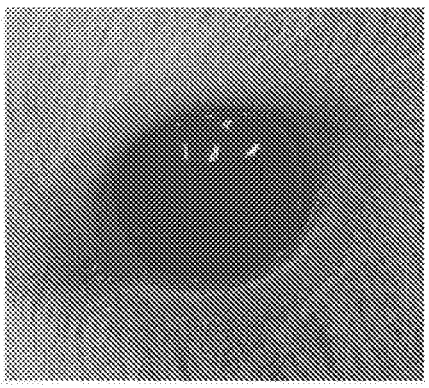
FIG. 1 is a photograph of an anterior eye segment of a guinea pig into which each test sample has been continuously instilled.
Figure 1:
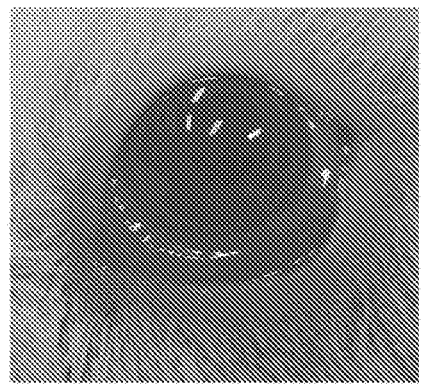
Figure 1:
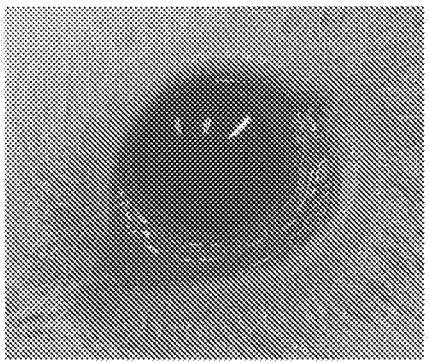
Figure 1:
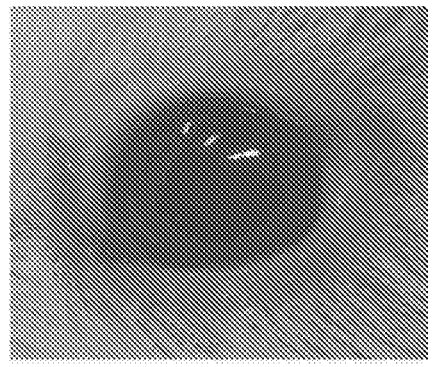

Hereinafter, preferred embodiments of the present invention will be described, but the present invention is not limited these embodiments.

[A. Immunogenic Composition]

An immunogenic composition of the present invention includes: a peptide hydrogel containing a positively or negatively charged self-assembling peptide and an aqueous medium; and an antigen, in which the self-assembling peptide is not covalently bonded to the antigen. The description that the "self-assembling peptide is not covalently bonded to the antigen" means that the self-assembling peptide is not intentionally covalently bonded to the antigen, and the presence of a slight covalent bond that can unintentionally occur depending on a pH environment, a storage environment, or the like is not excluded. As is apparent from the description of the entire specification, a peptide hydrogel and an antigen are not separately present in the immunogenic composition of the present invention, but are present in a state in which the antigen is integrated in the hydrogel. Accordingly, in other words, it can be said that the immunogenic composition of the present invention is a "gel-like immunogenic composition containing a positively or negatively charged self-assembling peptide, an aqueous medium, and an antigen, in which the self-assembling peptide is not covalently bonded to the antigen."

Due to the inclusion of the peptide hydrogel, the above-described immunogenic composition is also typically a gel. However, a peptide hydrogel is formed by self-assembling through a non-covalent bond of a self-assembling peptide, and can temporarily take the form of a sol due to physical stimulation such as stirring, vibration, and application of shearing. For this reason, the above-described immunogenic composition can also be turned into a sol in response to physical stimulation, and can then gel again over time. Accordingly, the immunogenic composition of the present invention may be in a fluid state as long as it has a gelling ability. In the present specification, a gel means a colloidal dispersion system solidified into a jelly. In one embodiment, a gel is a sol which has lost fluidity, and can maintain its shape against gravity.

The storage elastic modulus of the immunogenic composition measured using a rotary rheometer under a temperature condition of 37° C. is, for example, greater than or equal to 10 Pa, preferably greater than or equal to 50 Pa, more preferably greater than or equal to 100 Pa, and still more preferably greater than or equal to 200 Pa, and is, for example, less than or equal to 2,000 Pa, preferably less than or equal to 1,500 Pa, and more preferably less than or equal to 1,000 Pa.

The pH of the immunogenic composition is preferably set to a pH at which the charge of a self-assembling peptide is maintained at a physiological pH (7.4) (as a result, a pH at which a peptide hydrogel is positively or negatively charged). The pH can be, for example, 5.0 to 9.0 and preferably 5.5 to 8.5.

A-1. Peptide Hydrogel

A peptide hydrogel is a gel (self-assembling peptide gel) which contains a positively or negatively charged self-assembling peptide and an aqueous medium and is formed through self-assembling of the self-assembling peptide in the aqueous medium. Due to the inclusion of the positively or negatively charged self-assembling peptide, the peptide hydrogel can be positively or negatively charged as a whole gel.

In the above-described immunogenic composition, the peptide hydrogel functions as an adjuvant which enhances an immune response to an antigen. Although the reason why such an effect is exhibited is unclear, it is considered that this is because the peptide hydrogel can hold an antigen in the interior or on the surface of an administration site for a long period of time.

A-1-1. Self-assembling Peptide

In the present specification, a self-assembling peptide means a peptide that can spontaneously assemble in an aqueous solution through an interaction between peptide molecules to form a nanofiber. The interaction between peptide molecules is not particularly limited, but includes, for example, a hydrogen bond, an interionic interaction, an electrostatic interaction such as van der Waals force, and a hydrophobic interaction. The formation of a nanofiber can be checked through, for example, electron microscope observation.

A peptide that self-assembles through formation of a β-sheet structure consisting of a surface with relatively high hydrophilicity and a surface with relatively low hydrophilicity, preferably a β-sheet structure consisting of a hydrophobic surface on which only hydrophobic amino acid residues are disposed and a hydrophilic surface containing polar amino acid residues can be used as a self-assembling peptide, for example. Specific examples of such a self-assembling peptide include: a peptide consisting of 2N or (2N-1) amino acid residues in which amino acid residues at the 2n-th position are all hydrophobic amino acid residues and 33% or more, preferably 50% or more, and more preferably 60% or more of amino acid residues at the (2n-1)-th position are polar amino acid residues; and a peptide consisting of 2N or (2N-1) amino acid residues in which amino acid residues at the (2n-1)-th position are all hydrophobic amino acid residues and 33% or more, preferably 50% or more, and more preferably 60% or more of amino acid residues at the 2n-th position are polar amino acid residues (where n is a natural number from 1 to N).

Such a self-assembling peptide described above self-assembles in an aqueous solution so that two β-sheets elongate in an overlapping state with hydrophobic surfaces inside to form a nanofiber. The nanofiber can gel by further assembling due to an interaction between the hydrophilic surfaces and forming a network structure. The formation of the β-sheet structure can be confirmed by, for example, measuring a molar ellipticity through a circular dichroism measurement method and confirming that the molar ellipticity at 216 nm reaches a negative value. In addition, the formation of the β-sheet structure can also be confirmed by detecting a peak appearing around 1,620 $cm^{-1}$ due to β-sheets or a peak appearing around 1,690 $cm^{-1}$ due to antiparallel β-sheets through FT-IR analysis.

The above-described hydrophobic amino acids include non-polar amino acids such as alanine (Ala/A), leucine (Leu/L), isoleucine (Ile/I), valine (Val/V), methionine (Met/

M), phenylalanine (Phe/F), tryptophan (Trp/W), glycine (Gly/G), and proline (Pro/P). Among these, alanine, leucine, isoleucine, and valine are preferable, alanine and leucine are more preferable, and leucine is still more preferable.

The above-described polar amino acids include, as charged amino acids, basic amino acids such as arginine (Arg/R), lysine (Lys/K), and histidine (His/H) and acidic amino acids such as aspartic acid (Asp/D) and glutamic acid (Glu/E). The non-charged polar amino acids such as tyrosine (Tyr/Y), serine (Ser/S), threonine (Thr/T), asparagine (Asn/N), glutamine (Gln/Q), and cysteine (Cys/C) are also included in the polar amino acids.

The above-described self-assembling peptide has a positive or negative charge in an immunogenic composition. A self-assembling peptide having a charge of +1 to +3 or −1 to −3, preferably +2, +3, −2, or −3, more preferable +3 or +2 per molecule at a physiological pH can be preferably used as such a self-assembling peptide, for example. Such a self-assembling peptide can suitably form a nanofiber or a gel. In addition, since the self-assembling peptide can exhibit a reversible self-assembling ability in which fluidity increases due to physical stimulation such as stirring, vibration, or application of a shearing force and decreases due to stoppage of the physical stimulation, the self-assembling peptide can also be suitably used for administration such as instillation, spraying, and injection. In addition, according to a self-assembling peptide having no charge at a physiological pH, the type of antigen from which an effect of increasing immunogenicity can be obtained is sometimes limited. However, according to a self-assembling peptide having a charge, an effect of increasing immunogenicity with respect to various antigens can be obtained. Although not limiting the present invention, it is inferred that the reason why such an effect can be obtained is because a gel formed by a self-assembling peptide having a charge, particularly a positive charge, has excellent retentivity on the surfaces of cells and mucous membranes, in the subcutaneous tissue, and the like.

The charge of the above-described self-assembling peptide means a sum of charges of amino acid residues contained in the peptide molecules. The charge at a physiological pH can be calculated using, for example, a program available on the PROTEIN CALCULATOR v3.4 website (http://protcalc.sourceforge.net/).

The number of ammo acid residues constituting the above-described self-assembling peptide is, for example, 8 to 60, preferably 10 to 40, more preferably 10 to 32, and still more preferably 12 to 32. An N-terminal amide group and/or a C-terminal carboxyl group of the peptide may be appropriately protected by a protecting group such as an acetyl group or an amide group.

Examples of the above-described self-assembling peptide include a peptide consisting of the following amino acid sequence (A). In the peptide, the N-terminal amide group may be acetylated or the C-terminal carboxyl group may be amidated as necessary.

Amino acid sequence (A): $a_1b_1c_1b_2a_2b_3db_4a_3b_5c_2b_6a_4$, (In the amino acid sequence, $a_1$ to $a_4$ each represent a basic amino acid residue; $b_1$ to $b_6$ each represent a non-charged polar amino acid residue and/or a hydrophobic amino acid residue, provided that at least five thereof each represent a hydrophobic amino acid residue; $c_1$ and $c_2$ each represent an acidic amino acid residue; and d represents a hydrophobic amino acid residue or a non-charged polar amino acid residue.)

In one embodiment, $b_1$ to $b_6$ in the above-described amino acid sequence are all hydrophobic amino acid residues. $b_1$ to $b_6$ can each independently represent an alanine residue, a valine residue, a leucine residue, or an isoleucine residue, and preferably an alanine residue or a leucine residue. It is more preferable that $b_1$ to $b_6$ all be leucine residues, or that five be leucine residues and one be an alanine residue.

In one embodiment, d in the above-described amino acid sequence is an alanine residue, a leucine residue, an asparagine residue, a serine residue, or a glutamine residue.

In one embodiment, $a_1$ to $a_4$ in the above-described amino acid sequence are all arginine or lysine and preferably arginine.

in one embodiment, $c_1$ and $c_2$ in the above-described amino acid sequence are all aspartic acid or glutamic, acid, and preferably aspartic acid.

The self-assembling peptide that can be used in the present invention is not limited to the peptide consisting of the above-described amino acid sequence (A). For example, peptides disclosed in WO2007/000979 can be applied to the present invention.

Specific examples of the above-described self-assembling peptide include peptides shown in SEQ ID Nos: 1 to 16. The self-assembling peptide may be used alone or in a combination of two or more thereof within a range where the effect of the present invention can be obtained.

TABLE 1

| Amino acid sequence | Charge at pH 7.4 | SEQ ID No |
|---|---|---|
| n-RLDLRLALRLDLR-c | +2 | 1 |
| n-RLDLRLLLRLDLR-c | +2 | 2 |
| n-RADLRLALRLDLR-c | +2 | 3 |
| n-RLDLRLALRLDAR-c | +2 | 4 |
| n-RADLRLLLRLDLR-c | +2 | 5 |
| n-RADLRLLLRLDAR-c | +2 | 6 |
| n-RLDLRALRLRLDLR-c | +2 | 7 |
| n-RLDLRLLARLDLR-c | +2 | 8 |
| n-LELSLELSLELS-c | −3 | 9 |
| n-SLDLKLDLSLDL-c | −2 | 10 |
| n-SAEAKAEASAEAKAEA-c | −2 | 11 |
| n-SAEASAEASAEAKAEA-c | −3 | 12 |
| n-RLNLRLDLRLNL-c | +2 | 13 |
| n-RAQARAQARAQARAQA-c | +4 | 14 |
| n-RLDLRLSLRLDLR-c | +2 | 15 |
| n-RLDLRLNLRLDLR-c | +2 | 16 |

The formulation amount of the self-assembling peptide can be set so that the concentration of the self-assembling peptide in the above-described immunogenic composition becomes 0.1 w/v % to 5.0 w/v %, preferably 0.2 w/v % to 3.0 w/v %, more preferably 0.3 w/v % to 2.0 w/v %, and still more preferably 0.4 w/v % to 1.5 w/v %.

A-1-2. Aqueous Medium

Examples of an aqueous medium include water, physiological saline, buffered saline, a phosphate buffer solution, an isotonic aqueous buffer solution, and a mixed aqueous solution with a lower alcohol such as ethanol. The aqueous medium can further contain a pharmaceutically acceptable additive as necessary. The additive can be appropriately selected by those skilled in the art depending on the application of the immunogenic composition, preparations, and the like. Examples of the additive include a pH adjusting agent, an isotonic agent, a preservative, an excipient, a stabilizer, a filler, and a solubilizer. The additive may be used alone or in a combination of two or more thereof.

Examples of pH adjusting agents include citric acid, trisodium citrate, succinic acid, monosodium succinate, disodiurn succinate, sodium. acetate, sodium hydrogen carbonate, sodium carbonate, phosphoric acid, disodium hydrogen phosphate, sodium dihydrogen phosphate, histidine, and lysine.

Examples of isotonic agents include sodium chloride, polyethylene glycol, dextran, mannitol, sorbitol, inositol, glucose, fructose, lactose, xylose, mannose, maltose, sucrose, trehalose, and raffinose.

A-2. Antigen

The above-described antigen is a substance having immunogenicity. The antigen can be a peptide, a protein (including a glycoprotein and a lipoprotein), a nucleotide, a carbohydrate, and a lipid (including a glycolipid and a phospholipid) or derivatives thereof, and is preferably a protein. The antigen may be used alone or in a combination of two or more thereof.

The molecular weight (kDa) of the above-described antigen is, for example, greater than or equal to 6.0, preferably greater than or equal to 8.0, and more preferably greater than or equal to $1.0 \times 10$. The molecular weight of antigen can be set to be, for example, less than or equal to $1.0 \times 10^3$.

The above-described antigen can be appropriately selected depending on the application of the immunogenic composition, the purposes, and the like. For example, in a case where the immunogenic composition is used for treating or studying allergic diseases, the antigen includes an antigen (allergen) causing the allergic diseases.

As the antigen causing allergic diseases, a dietary one or a respirable one may be used. A dietary antigen is generally derived from a food, and specific examples thereof include an antigen of an egg allergy (for example, ovalbumin, ovomucoid, lysozyme, or ovotransferrin), an antigen of a milk allergy (for example, casein, α-lactoglobulin, or β-lactoglobulin), an antigen of a wheat allergy (for example, gluten, gliadin, or glutenin), an allergen of a peanut allergy (for example, Ara h1), and an allergen of a fish allergy (for example, Gad c1 derived from codfish). A respirable antigen can be derived from a mite, house dust, plants (such as pollen), animals (such as hair and skin components), and specific examples thereof include an antigen of a mite allergy (for example, Der f1, Der p1, Der f2, Der p2), and an antigen of a cockroach allergy (for example, Bla g1). In addition, papain which is used as a model protein of a mite allergen can also he used as an antigen from the viewpoint that papain belongs to the same protein family (cysteine protease) as Der f1 and Der p1 and has a similar protein structure to them.

In addition, in a case where the immunogenic composition is used for, for example, preventing or treating an infectious disease, the antigen includes an antigen derived from a pathogen causing the infectious disease.

Examples of an antigen derived from a pathogen causing the infectious disease include: antigens derived from viruses such as influenza virus, hepatitis virus, human immunodeficiency virus (HIV), RS virus, rubella virus, measles virus, mumps virus, herpes virus, polio virus, rotavirus, Japanese encephalitis virus, varicella virus, adenovirus, rabies virus, and yellow fever virus; antigens derived from bacteria such as diphtheria *bacillus*, tetanus *bacillus Bordetella pertussis*, *Bacillus* influenzae, *Bacillus* tuberculosis, pneumococcus, *Helicobacter pylori*, anthrax *bacillus*, *Salmonella typhi*, meningococci, dysentery *bacillus*, and cholera vibrio; and antigens derived from fungi such as Candida fungus, Histoplasma fungus, Cryptococcus fungus, and Aspergillus fungus.

In one embodiment, an antigen contains a positively charged protein at a physiological pH. A self-assembling peptide having no charge at a physiological pH sometimes does not exhibit an effect of increasing the immunogenicity with respect to a positively charged protein at a physiological pH. However, since a self-assembling peptide having a charge can exhibit an effect of increasing the immunogenicity even with respect to a positively charged protein, the effect as an adjuvant can be more suitably obtained. The positively charged protein at a physiological pH can be a protein having an isoelectric point of greater than or equal to 7.5, preferably greater than or equal to 8.0, and more preferably greater than or equal to 8.5.

The formulation amount of an antigen in the above-described immunogenic compositioncan be, for example, $1.0 \times 10^{-3}$ mg/mL, to 10.0 mg/mL, preferably $1.0 \times 10^{-2}$ mg/mL to 5.0 mg/mL, and more preferably $5.0 \times 10^{-2}$ mg/mL to 1.0 mg/mL.

[B. Method for Producing Immunogenic Composition]

The above-described immunogenic composition can be obtained by, for example, mixing a peptide composition containing a self-assembling peptide and an aqueous medium with an antigen or an aqueous antigen solution or mixing a self-assembling peptide, an aqueous medium, and an antigen or an aqueous antigen solution. As described above, although the immunogenic composition immediately after the mixing can have fluidity, it can then gel over time. Each component or the mixture before mixing may be sterilized as necessary. Any appropriate methods applicable in the technical field can be used as the mixing method and the sterilization method.

In one embodiment, a method for producing the above-described immunogenic composition includes: (A-I) a step of determining a combination of an antigen and a positively or negatively charged self-assembling peptide; and (A-II) a step of mixing an aqueous medium with the determined combination of the antigen and the self-assembling peptide.

The above-described combination of an antigen and a positively or negatively charged self-assembling peptide is not particularly limited, but in a case where the antigen has a protease activity, a self-assembling peptide having low susceptibility to the protease activity is preferably selected. in addition, in a case where the antigen contains a positively or negatively charged protein at a physiological pH, a self-assembling peptide having a charge of preferably +2, +3, −2, or −3, more preferably +3 or +2 per molecule at a physiological pH is preferably selected.

The mixing of the determined combination of an antigen and a self-assembling peptide with an aqueous medium can be performed by mixing a peptide composition containing a self-assembling peptide and an aqueous medium with an antigen or an aqueous antigen solution or mixing a self-assembling peptide, an aqueous medium, and an antigen or an aqueous antigen solution as described above.

[C. Method for Using Immunogenic Composition]

The above-described immunogenic composition can be used for the purposes of, for example, providing immunity (acquired immunity) to a target antigen and inducing a decrease (hyposensitization) in an immune response or non-response (desensitization) to a target antigen with respect to an individual of a subject to be inoculated. For inoculation (administration) of an immunogenic composition, inoculation methods such as percutaneous, intramuscular, intravenous, intraperitoneal, and transmucosal (oral, nasal, sublingual, instillation, or enteral) inoculation can be employed, for example.

The subject to be inoculated is not particularly limited, and examples thereof include humans and various non-human animals (such as monkeys, chimpanzees, pigs, cow, horses, goats, sheep, chickens, quails, ducks, ostriches, dogs, cats, hamsters, mice, rats, guinea pigs, and rabbits).

The self-assembling peptide used in the above-described immunogenic composition can typically reversibly self-assemble (gel). For this reason, even in a case where the viscosity of the immunogenic composition becomes high due to self-assembling of the self-assembling peptide, the viscosity can be lowered by applying a shearing force, and administration through injection, instillation, spraying, or the like can be easily performed. The administered immunogenic composition can self-assemble again at an administration site to present antigens over a longer period of time at the administration site.

The above-described immunogenic composition may be produced and preserved as a dry product containing no solvent. The immunogenic composition in a dry state can be used (administered) after adding an aqueous medium and mixing it with the dry immunogenic composition to make an aqueous composition (which may be a sol or a gel).

EXAMPLES

Hereinafter, the present invention will be described in detail with reference to examples, but is not limited to these examples. A measurement method and an evaluation method used in the examples are as follows.

<Method for Measuring Storage Elastic Modulus>

A storage elastic modulus G' of a sample was measured using a rotary rheometer (TA instruments, product name: "ADVANCED RHEOMETER AR 1000") which is a dynamic viscoelasticity measurement device. Specifics were as follows. First, a constant-temperature tank for keeping a sample table and a geometry (an aluminum cone with a diameter of 20 mm, a cone angle of 1°, and a gap of 24 μm) to be brought into contact with a sample at a constant temperature was attached to the rheometer. Next, the storage elastic modulus of one sample was measured three times under the measurement conditions of a temperature of 37° C., a torque of 1 μN·m, and a frequency of 0.5 rad/s to 100 rad/s in the following measurement procedures, and an average value of the values when the frequency was 1 rad/s was regarded as the storage elastic modulus G'.

(1) 55 μL of a sample is placed on a sample table of a rheometer using a pipette.

(2) The geometry is moved to have a gap of 24 μm from the sample table to be brought into contact with the sample.

(3) The geometry is slightly moved to be applied to the sample.

(4) Measurement is started 15 seconds (a solvent trap for preventing a solvent from volatilizing from the sample is attached during the 15 seconds) after the movement of the geometry is stopped.

<Method for Measuring pH>

The pH was measured with a portable pH meter (manufactured by HORIBA, Ltd., product number "B-71.2").

[Preparation of Peptide Composition]

1. Peptide Composition A:

A trade name "Panacea Gel" (which was manufactured by Menicon Co., Ltd. and was a high pressure steam sterilized peptide composition containing a 1.5 w/v % self-assembling peptide (Ac-RLDLRLALRLDLR-CONH$_2$ (SEQ ID No: 1)), an isotonic agent, a pH adjusting agent, and water, and had a pH of 5.9 and a storage elastic modulus of 515.5 Pa) was used as a peptide composition A.

2. Peptide Compositions B to D:

Components were mixed with each other according to the composition shown in Table 2, dissolved, and high pressure steam sterilized at 121° C. for 20 minutes to obtain peptide compositions B to D. Storage elastic moduli of the peptide compositions B and C prepared using peptides of SEQ ID Nos: 15 and 16 were respectively 704.7 Pa and 578.5 Pa. On the other hand, the storage elastic modulus of the peptide composition D prepared using a peptide of SEQ ID No: 17 was 73.4 Pa.

TABLE 2

| | Peptide (manufactured by Menicon Nect Co., Ltd.) | Isotonic agent | pH Adjusting agent | Injection water | pH |
|---|---|---|---|---|---|
| B | Ac-RLDLRLSLRLDLR-CONH$_2$ (SEQ ID No: 15) | 1.5 (w/v %) | 7.2 (w/v %) | 0.47 (w/v %) | Residue | 6.1 |
| C | Ac-RLDLRLNLRLDLR-NH$_2$ (SEQ ID No: 16) | | | | | 5.9 |
| D | Ac-RLDLRLA-CONH$_2$ (SEQ ID No: 17) | | | | | 6.1 |

Example 1

Test samples shown in Table 3 were instilled at a dosage of 10 μL per eye of female Hartley guinea pigs (supplied by Japan SLC, Inc.) up to day 21 at a frequency of 4 to 5 times a week while considering the first day of administration as day 1, and the conditions of anterior eye segments were observed (N=1). Photographs of the anterior eye segments imaged on day 21 after the instillation are shown in FIG. 1.

TABLE 3

| Test sample | Preparation method | Form after 15 minutes of mixing | pH |
|---|---|---|---|
| 1 | Physiological saline and OVA aqueous solution (0.5 mg/mL) were mixed with each other in equal amounts | Solvent | 6.1 |
| 2 | Freund's Complete adjuvant (manufactured by BD) and OVA aqueous solution (0.5 mg/mL) were mixed with each other in equal amounts | Solvent | 5.7 |

TABLE 3-continued

| Test sample | Preparation method | Form after 15 minutes of mixing | pH |
|---|---|---|---|
| 3 | Peptide composition A and OVA aqueous solution (0.5 mg/mL) were mixed with each other in equal amounts | Gel | 6.1 |
| 4 | Peptide composition A was used as it is | Gel | 5.9 |

OVA: Ovalbumin (isoelectric point: 4.5, manufactured by Wako Pure Chemical Industries, Ltd., Cat. No.

As shown in FIG. 1, in the individual into which a test sample 1 was instilled, there was no particular reaction in the anterior eye segment after the continuous instillation, and neither hyperemia nor lacrimation was observed. In the individual into which a test sample 2 was instilled, the guinea pig gradually blinked and half-closed its eyes from day 7 of the instillation, and these reactions after the instillation became remarkable with the lapse of days. On day 21 of the instillation, edema of the sclera and conjunctiva, hyperemia, and lacrimation were observed 5 minutes after the instillation. In the individual into which a test sample 3 was instilled, the guinea pig gradually blinked and half-closed its eyes from day 14 of the instillation. However, both the reactions were milder than those of the individual into which the test sample 2 was instilled. On day 21 of the instillation, edema of the sclera and conjunctiva, hyperemia, and lacrimation were observed 5 minutes after the instillation, and symptoms similar to those of the individual into which the test sample 2 was instilled were recognized. In the individual into which a test sample 4 was instilled, reactions such as hyperemia and lacrimation were not recognized whereas blinking was observed several times immediately after the instillation.

From the above-described findings, the blinking immediately after the instillation of the peptide composition A is due to physical stimulation by gel instillation. It is inferred that, in a case where the peptide composition A is used in a transmucosal vaccine, the peptide composition has an effect of promoting production of an antibody to an antigen without causing production of an antibody to itself.

Example 2

Figure 2:
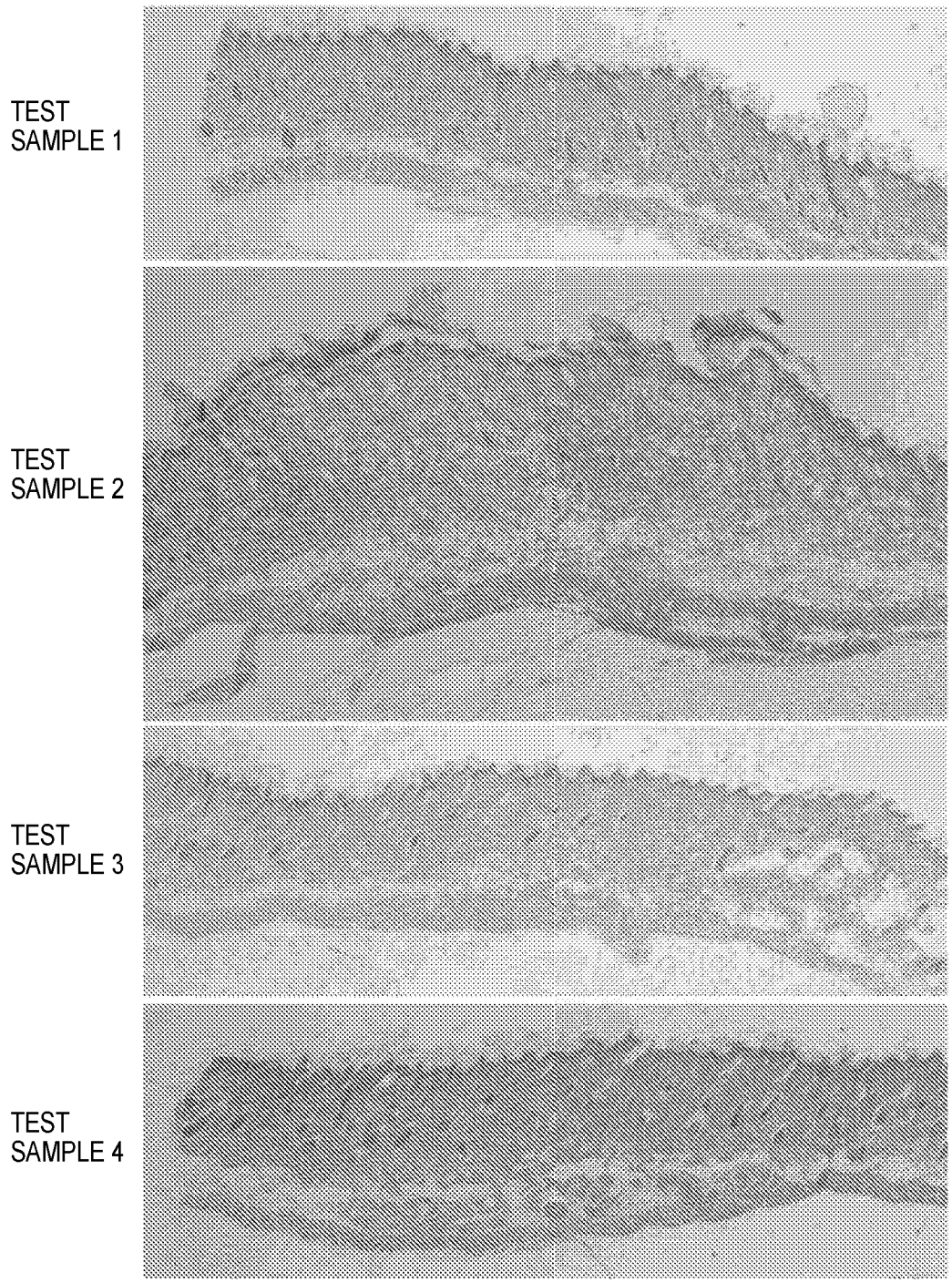
FIG. 2 shows images of tissue specimens of the backs which have been prepared after the first administration.

0.1 mL of each of the test samples shown in Table 3 was intradermally administered to 2 sites of the back of each female Hartley guinea pig (supplied by Japan SLC, Inc.) of a single-dose group, and the female Hartley guinea pigs were euthanized on day 3 after the administration (N=1). Thereafter, the skin at the administration site was collected to prepare a tissue specimen, and the presence or absence of an inflammatory response and an immune response was observed. Images of tissue specimens of the backs which have been prepared after the first administration are shown in FIG. 2. 0.1 mL of each of the test samples shown in Table 3 was intradermally administered to 2 sites of the back of each female Hartley guinea pig (supplied by Japan SLC, Inc.) of a double-dose group on days 1 and 8, and the female Hartley guinea pigs were euthanized on day 6 after the second administration (N=1). Thereafter, the skin at the administration site was collected to prepare a tissue specimen, and the presence or absence of an inflammatory response and an immune response was observed. Images of tissue specimens of the backs which have been prepared after the second administration are shown in FIG. 3.

As a result of observation of the tissue specimens after the first administration, no abnormality was observed in the epithelium and no cell infiltration was recognized in the individual, to which the test sample 1 was administered, as shown in FIG. 2. In the individual to which the test sample 2 was administered, the epidermis was remarkably thickened, and multilocular blisters were observed. In addition, a large number of cells were recognized in the administration site. In the individual to which the test sample 3 was administered, a state in which the epidermis was slightly thickened, the test sample 3 remained around the administration site, and cells accumulated was observed. Similarly, in the individual to which the test sample 4 was administered, thickening of the epidermis and remaining of the test sample 4 were recognized, and a state in which cells accumulated was observed. From the above, it was considered that the peptide composition A serves to attract inflammatory cells.

Figure 3:
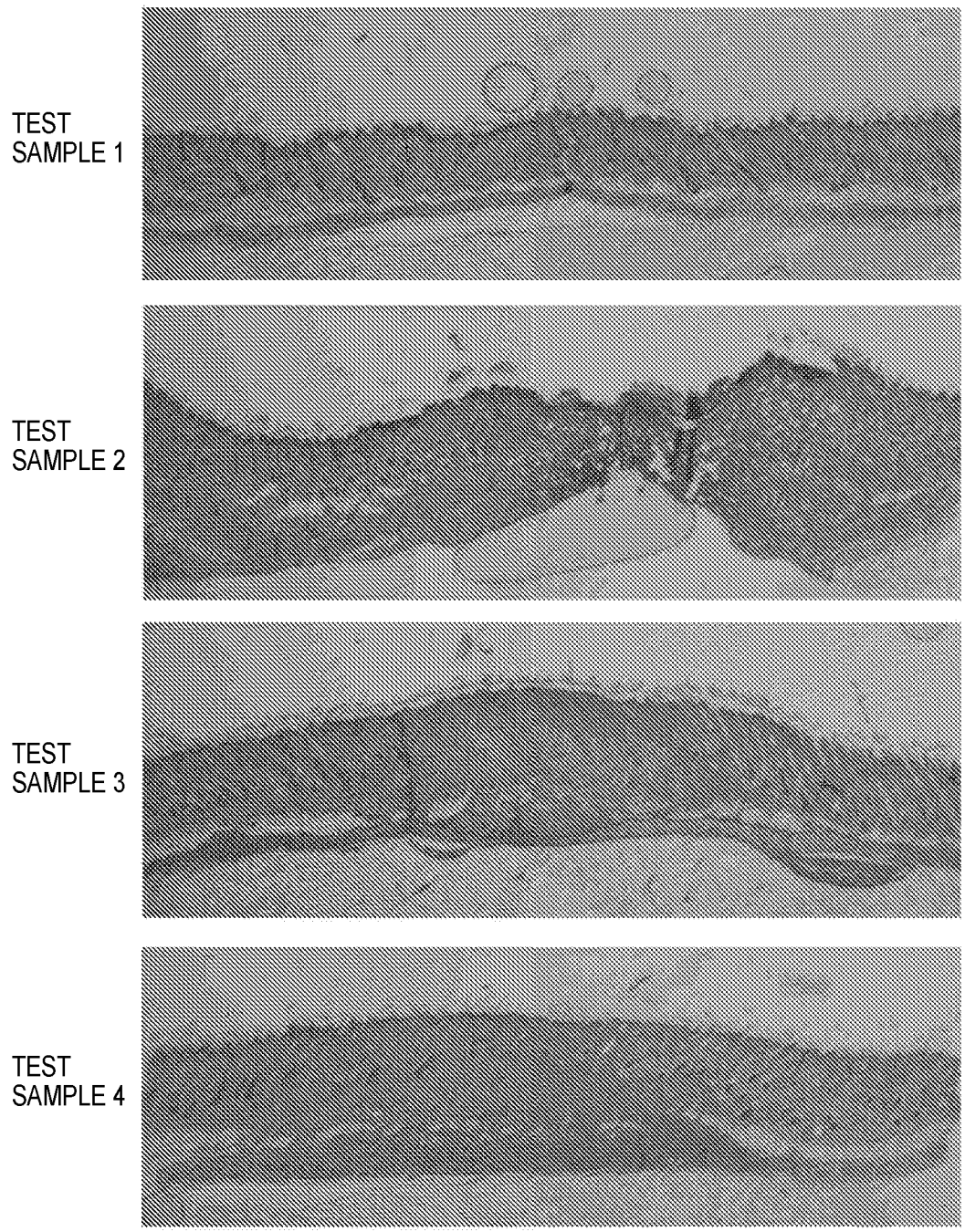
FIG. 3 shows images of tissue specimens of the backs which have been prepared after the second administration.

In addition, as shown in FIG. 3, no abnormality was observed in the epithelium and only very slight cell infiltration was recognized in the individual of the double-dose group to which the test sample 1 was administered. On the other hand, in the individual to which the test sample 2 was administered, the skin contracted, a scab was formed, and cells intradermally accumulated. In the individual to which the test sample 3 was administered, a state in which the epidermis was remarkably thickened and many cells accumulated around the administration site was observed, but neither formation of scabs nor tissue hardening was recognized. In both of the individuals to which the test samples 2 and 3 were administered, many antigen-presenting cells and inflammatory cells accumulated compared to those of the single-dose group, and therefore, it was considered that the immune response is enhanced. From this, it was considered that the peptide composition A has the same adjuvant ability as that of a Freund's complete adjuvant (FCA), but does not cause any damage to the skin structure, for example, formation of scabs or tissue hardening. In the individual to which the test sample 4 was administered, thickening of the epidermis was not observed, but a smaller number of cells than those of the individual to which the test sample 3 was administered accumulated. In addition, the degree of cell infiltration was the same as that of the single-dose group, and the immune response was not enhanced by the double dose. From this, it was considered that the peptide composition A temporarily causes inflammation immediately after he administration, but s not antigenic in itself. It was suggested that the peptide composition A causes inflammation for several days after administration, which promotes accumulation of antigen-presenting cells to effectively incorporate antigens or produce antibodies.

Example 3

Three-week-old female BALB/c mice (supplied by Charles River) were divided into 4 groups of 6 mice and sensitized as shown in Table 4. Specifically, 50 µL of a test sample was intradermally administered to two sites of the back on days 0 and 7 of administration, and blood was collected from the inferior vena cava of half of the mice in each group on day 14 (intradermally administration was not performed for an untreated group). For the remaining mice in each group, 5 µL of a 2 mg/10 µL OVA solution was nasally administered to both nostrils frequency of 3 to 4 times/week from day 14 to day 27, and blood was collected from the inferior vena cava on day 28 (24 hours after the final nasal drip).

TABLE 4

| Administration group | Intradermal administration of test sample on days 0 and 7 | Nasal administration of test sample on days 14 to 27 (induction) |
|---|---|---|
| A-1 | Test sample 1: Mixture of physiological saline and OVA aqueous solution (0.5 mg/mL) in equal amounts | None<br>OVA aqueous solution (2 mg/10 μL) |
| A-2 | Test sample 3: Mixture of peptide composition A and OVA aqueous solution (0.5 mg/mL) in equal amounts | None<br>OVA aqueous solution (2 mg/10 μL) |
| A-3 | Mixture of 20 mg/mL of Imject Alumn (manufactured by Thermo Fisher Scientific Inc.) and OVA aqueous solution (0.5 mg/mL) in equal amounts | None<br>OVA aqueous solution (2 mg/10 μL) |
| Untreated group | None | None<br>OVA aqueous solution (2 mg/10 μL) |

The collected blood was not subjected to a heparin treatment, preserved overnight at 4° C., and centrifuged at 1,200 × g for 20 minutes at 4° C., and a supernatant (serum) was collected. IgG in the blood was measured using a product name "Mouse IgG-ELISA kit" (manufactured by Life Diagnostics, Inc.) The serum was diluted 200,000 times with a dilution buffer attached to the kit. The results are shown in Table 4.

Figure 4:
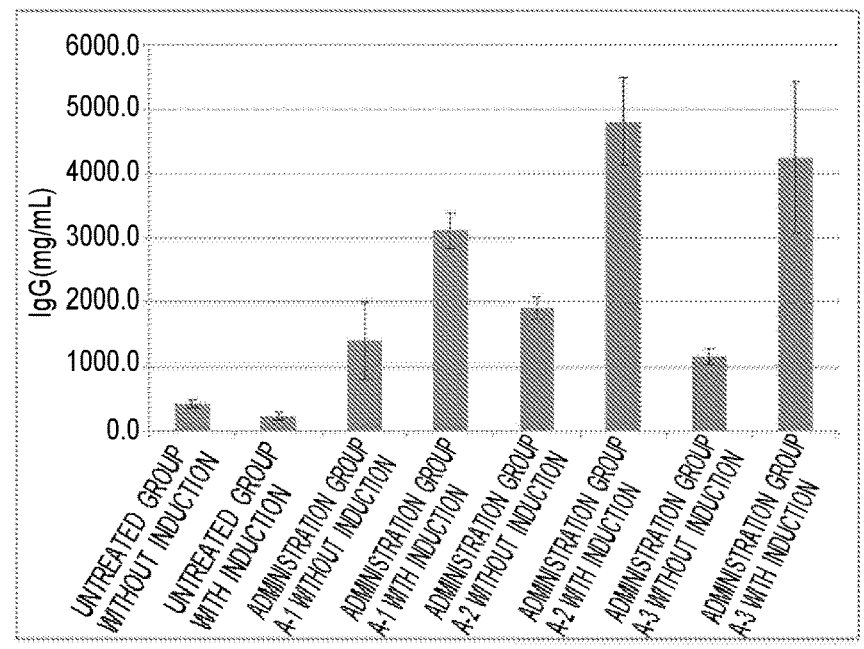
FIG. 4 is a graph showing blood IgG concentrations of mice to which each test sample has been administered.
Figure 5A:
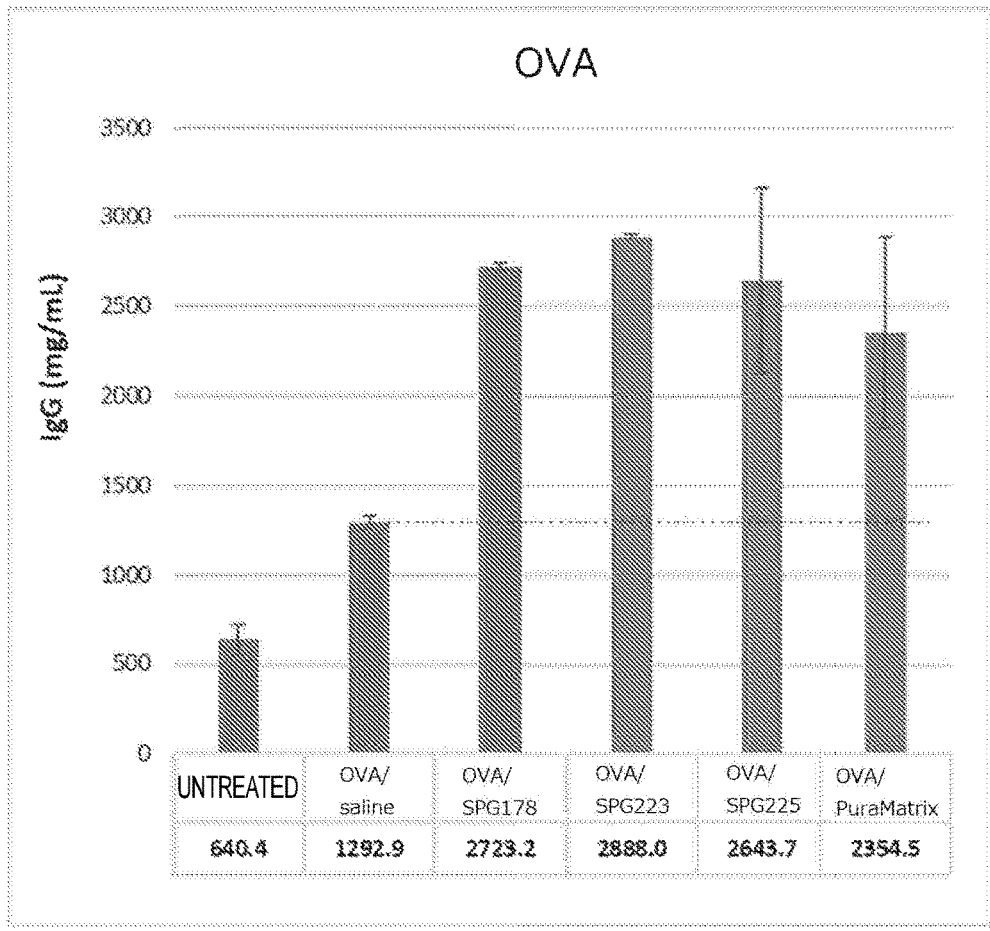
FIG. 5A is a graph showing blood IgG concentrations of ice to which each test sample has been administered.
Figure 5B:
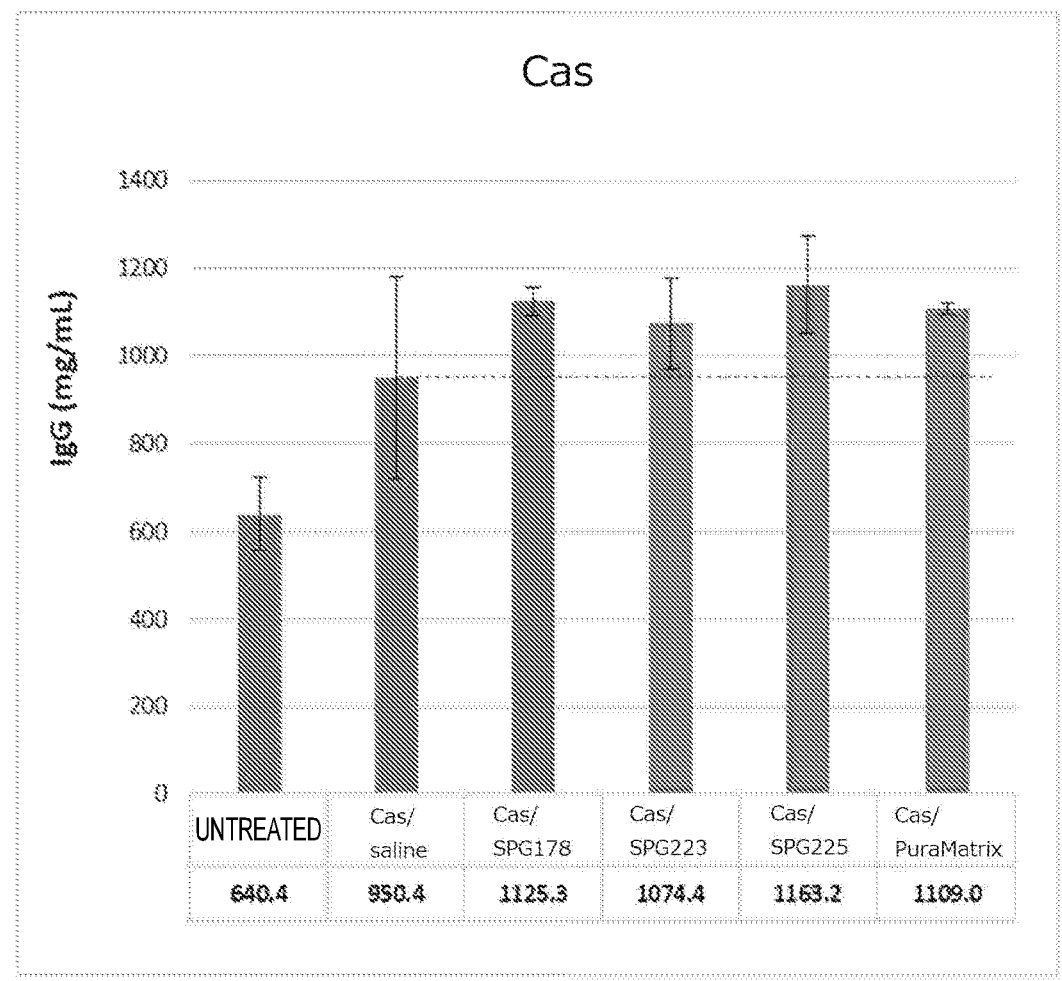
FIG. 5B is a graph showing blood IgG concentrations of rice to which each test sample has been administered.
Figure 5C:
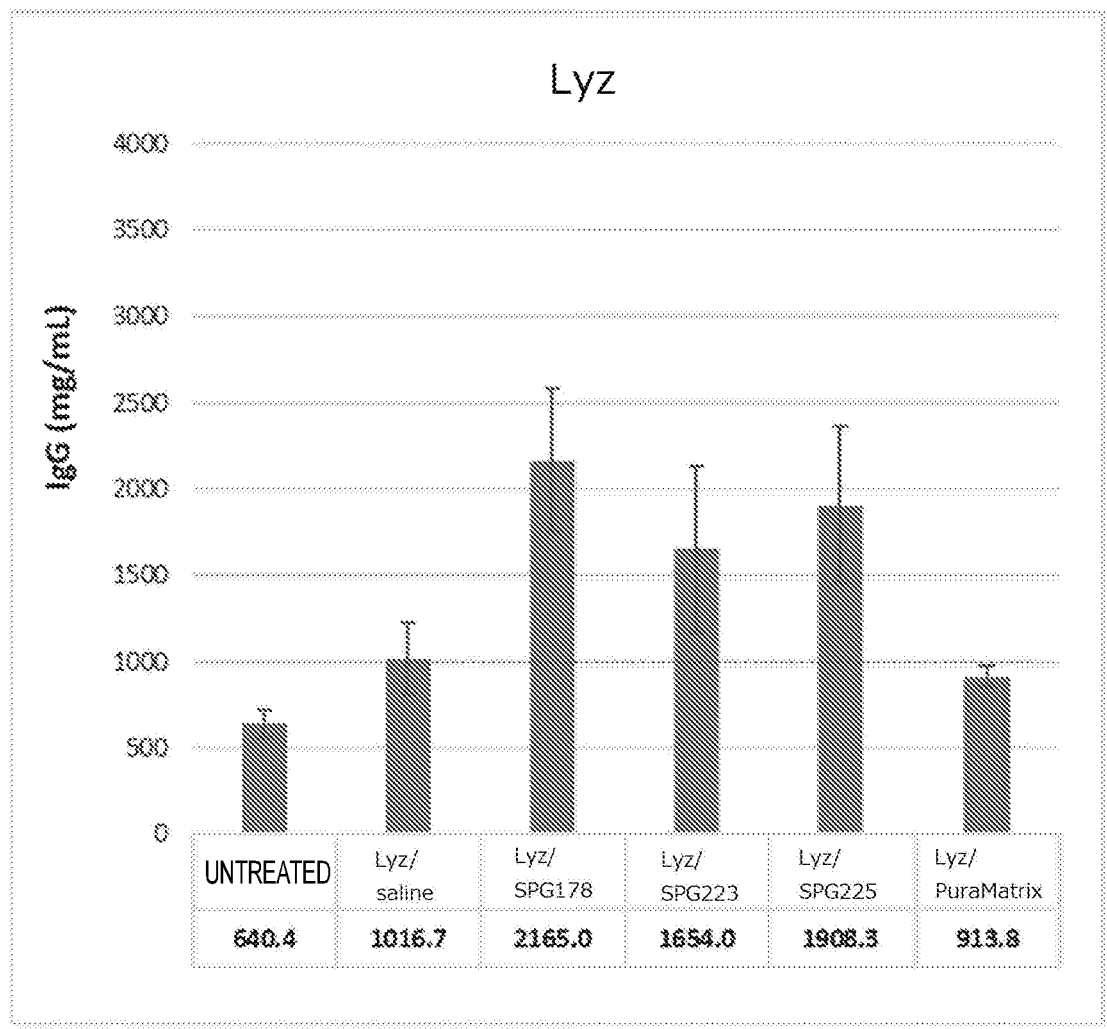
FIG. 5C is a graph showing blood IgG concentrations of mice to which each test sample has been administered.
Figure 5D:
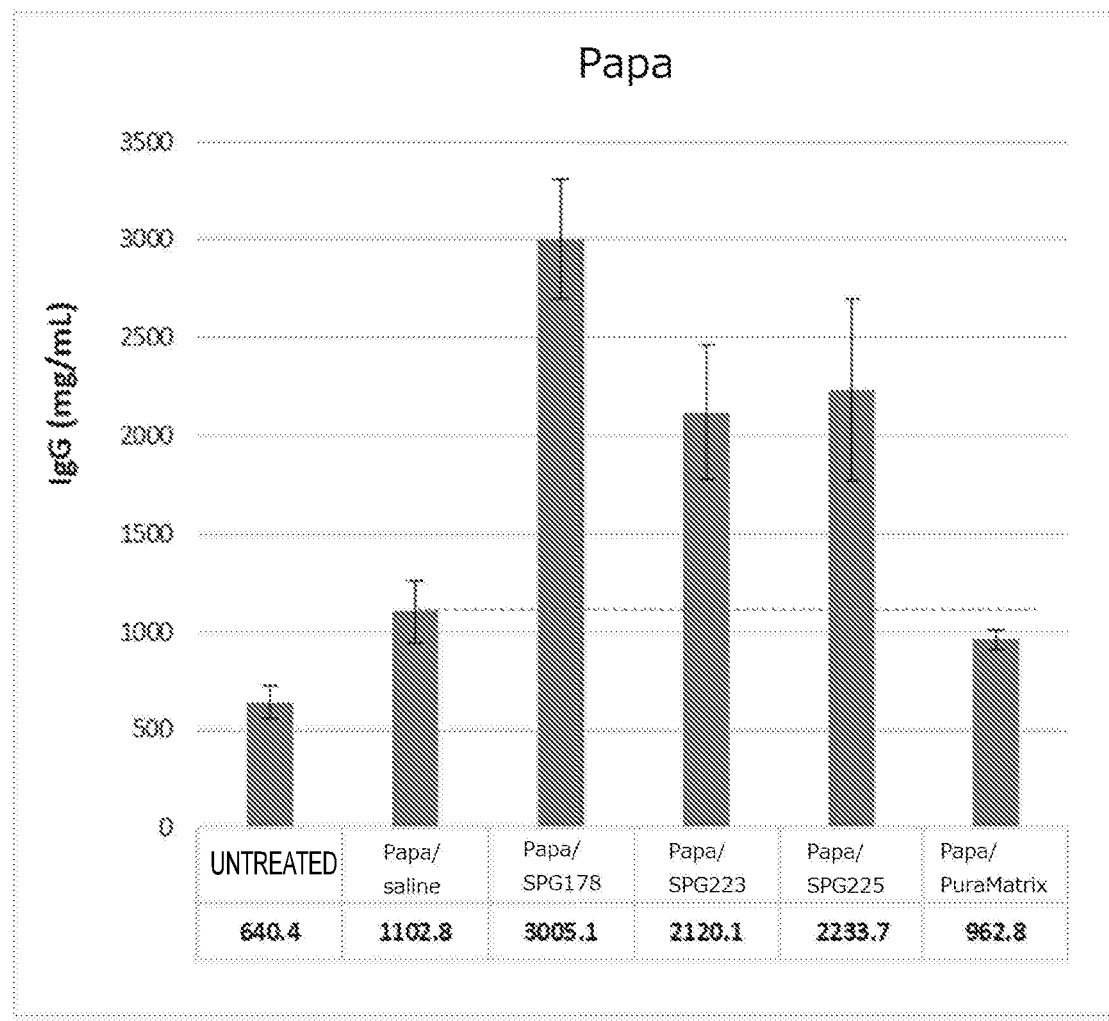
FIG. 5D is a graph showing blood IgG concentrations of mice to which each test sample has been administered.

As shown in FIG. 4, it can be seen that the value of the blood IgG concentration tends to be significantly higher after the induction (nasal administration) compared to that before the induction in all of the administration groups A-1 to A-3. The increase in IgG value was particularly large in the administration groups A-2 and A-3. The IgG concentration of the untreated group was lows and no increase in concentration even after the induction was recognized.

In addition, when the mice were observed, the inside of the back skin of the mice in the administration groups A-2 and A-3 was swollen and a scab was formed 1 week after the administration. On the other hand, there was no abnormality recognized in the mice in the administration group A-1 and the untreated group. Regarding the nasal administration, half-closed eyes, shaking, snorting, or a behavior such as damaging bedding were observed in all the groups since about day 4 of the administration. These symptoms started 4 to 5 minutes after the administration and were intermittently recognized for about 15 to 30 minutes. Although there was a tendency for the frequency to increase when the administration is continuously performed, no significant difference was recognized between the groups.

Example 4

Figure 6A:
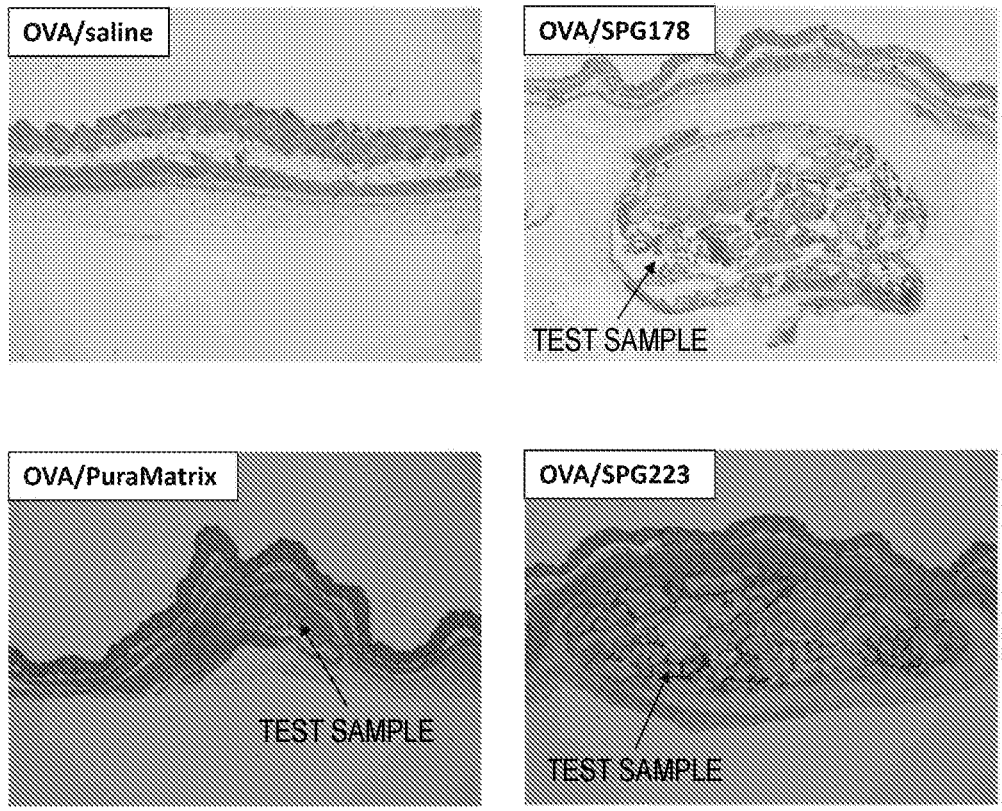
FIG. 6A shows images of tissue specimens of the backs of mice to which each test sample has been administered.
Figure 6B:
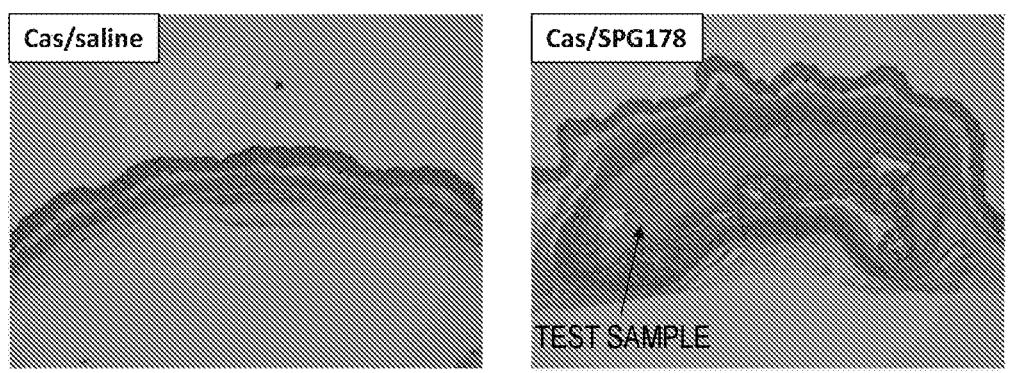
FIG. 6B shows images of tissue specimens of the backs of mice to which each test sample has been administered.
Figure 6C:
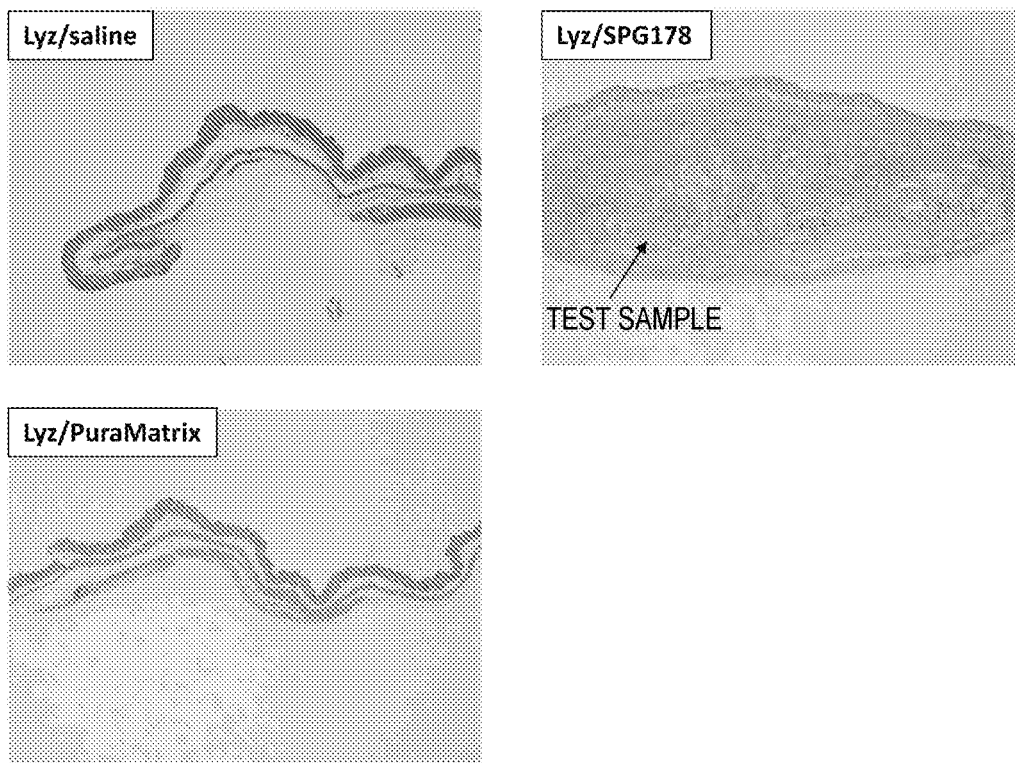
FIG. 6C shows images of tissue specimens of the backs of mice to which each test sample has been administered.

Five-week-old female BALB/c mice (supplied by Charles River) were divided into administration groups of 2 mice and an untreated group of 3 mice. 100 μL of each test sample described in Table 5 was intradermally administered to mice of corresponding groups on days 0, 7, and 14 of the administration. Blood was collected from the inferior vena cava of each mouse (including the untreated group) 7 days (on day 21 of the administration) after the third administration. The collected blood was incubated at 25° C. for 30 minutes and then preserved overnight at 4° C. to assemble a blood clot, centrifugation was performed at 1,000 to 1,200 × g at 4° C. for 20 minutes, and a supernatant was collected. The blood IgG value of the collected serum was measured using an IgG ELISA kit. The serum was diluted 200,000 times with a dilution buffer attached to the kit. The results are shown in FIGS. 5A to 5D. In addition, the back skin including the administration site of the third test sample was collected after collecting blood to prepare a tissue specimen. Tissue specimen images are shown in FIGS. 6A to 6C, The method for preparing the above-described test sample is as follows. That is, an antigen solution was prepared by dissolving an antigen protein in water, and the antigen solution and a 1.5 w/v % peptide composition (peptide compositions A to D described in Table 1) or PuraMatrix™ (which is manufactured by Corning Japan Ltd. and is a self-assembling peptide composition containing 1.0 w/v % of Ac-RADARADARADARADA-CONH$_2$ (SEQ ID No: 18)) were mixed with each other so that the self-assembling peptide concentration became 0.75 w/v % and the antigen protein concentration became 0.25 mg/mL (=0.025 w/v %) to prepare a test sample. In addition, a sample obtained by mixing the above-described antigen solution with physiological saline so that the antigen protein concentration became 0.25 mg/mL was used as a control sample.

TABLE 5

| | Test sample | | | | | |
|---|---|---|---|---|---|---|
| | Peptide | | Antigen | | | |
| Administration group | Type (SEQ ID NO) | Concentration (w/v %) | Type | Concentration (mg/mL) | pH | Form[*1] |
| OVA/saline | — | 0 | Albumin | 0.25 | 6.1 | Liquid |
| OVA/SPG178 | 1 | 0.75 | | | 6.1 | Gel |
| OVA/SPG223 | 15 | | | | 6.1 | Gel |
| OVA/SPG225 | 16 | | | | 5.9 | Gel |
| OVA/SPG204 | 17 | | | | 6.1 | Fluid |
| OVA/Puramatrix | 18 | | | | 5.6 | Gel |

TABLE 5-continued

| Administration group | Peptide Type (SEQ ID NO) | Concentration (w/v %) | Antigen Type | Concentration (mg/mL) | pH | Form[*1] |
|---|---|---|---|---|---|---|
| Cas/saline | — | 0 | Casein[*2] | 0.25 | 11.1 | Liquid |
| Cas/SPG178 | 1 | 0.75 | | | 6.4 | Gel |
| Cas/SPG223 | 15 | | | | 6.1 | Gel |
| Cas/SPG225 | 16 | | | | 6.3 | Gel |
| Cas/Puramatrix | 18 | | | | 5.6 | Gel |
| Lyz/saline | — | 0 | Lysozyme[*3] | 0.25 | 4.7 | Liquid |
| Lyz/SPG178 | 1 | 0.75 | | | 6.1 | Gel |
| Lyz/SPG223 | 15 | | | | 5.6 | Gel |
| Lyz/SPG225 | 16 | | | | 5.9 | Gel |
| Lyz/Puramatrix | 18 | | | | 4.4 | Gel |
| Papa/saline | — | 0 | Papain[*4] | 0.25 | 6.2 | Liquid |
| Papa/SPG178 | 1 | 0.75 | | | 6.1 | Gel |
| Papa/SPG223 | 15 | | | | 5.9 | Gel |
| Papa/SPG225 | 16 | | | | 6.0 | Gel |
| Papa/Puramatrix | 18 | | | | 5.5 | Gel |

[*1]Form after 15 minutes of mixing of protein solution with peptide composition
[*2]Casein (Isoelectric point = 4.6), manufactured by Wako Pure Chemical Industries, Ltd., Cat. No. 030-01505
[*3]Lysozyme (Isoelectric point = 11.1), manufactured by Wako Pure Chemical Industries, Ltd., Cat. No. 120-02674
[*4]Papain (Isoelectric point = 8.75), manufactured by Wako Pure Chemical Industries, Ltd., Cat. No. 164-00172

As shown in FIGS. 5A to 5D, the immunogenicity of self-assembling peptide gels of SEQ ID Nos: 1, 15, and 16 was enhanced even in a case where the self-assembling peptide gels were used in combination with any antigen protein. On the other hand, Puramatrix™ containing a self-assembling peptide of SEQ ID No: 18 exhibited an effect of enhancing the immunogenicity with respect to albumin and casein (all are negatively charged proteins at a physiological pH), but did not exhibit an effect of enhancing the immunogenicity with respect to lysozyme and papain (all are positively charged proteins at a physiological pH). Although not shown in the drawings, the blood IgG value of the group (OVA/SPG204) to which a fluid containing a self-assembling peptide of SEQ ID No: 17 was administered was the same as that of the OVA/saline group, and no effect of enhancing the immunogenicity was confirmed.

In addition, as shown in FIGS. 6A to 6C, in the inside of the skin of the mice to which a test sample containing a self-assembling peptide gel of SEQ ID No: 1 or 15 is administered, a state in which the test sample remained inside the skin was observed even 7 days after the administration. On the on the other hand, in the inside of the skin of the mice to which a test sample in which physiological saline was used or a test sample in which PuraMatrix™ was used was administered, remaining of a trace amount of test sample was recognized or no remaining of the test sample was recognized.

INDUSTRIAL APPLICABILITY

The present invention can be suitably used in the field of manufacturing pharmaceutical products.

What is claimed is:

1. An immunogenic composition for enhancing immune response of an antigen, comprising:
   a peptide hydrogel containing a positively or negatively charged self-assembling peptide and an aqueous medium; and
   an antigen,
   wherein the self-assembling peptide is not covalently bonded to the antigen,
   wherein the self-assembling peptide is a peptide having an amino acid sequence (A):
   a1b1c1b2a2b3db4a3b5c2b6a4,
   wherein a1 to a4 each represents a basic amino acid residue;
   b1 to b6 each represents a non-charged polar amino acid residue and/or a hydrophobic amino acid residue, provided that at least five thereof represent hydrophobic amino acid residues;
   c1 and c2 each represents an acidic amino acid residue; and d represents a hydrophobic amino acid residue or a non-charged polar amino acid residue, and
   wherein a storage elastic modulus of the immunogenic composition is 10 Pa to 2,000 Pa.

2. The immunogenic composition according to claim 1, wherein the self-assembling peptide has a charge of +3, +2, or +1 per peptide molecule at a physiological pH.

3. The immunogenic composition according to claim 1, wherein the self-assembling peptide has a charge of +3 or +2 per peptide molecule at a physiological pH.

4. The immunogenic composition according to claim 1, wherein the number of amino acid residues constituting the self-assembling peptide is 10 to 32.

5. The immunogenic composition according to claim 1, wherein a concentration of the self-assembling peptide contained in the immunogenic composition is 0.3 w/v % to 2.0 w/v %.

6. The immunogenic composition according to claim 1, wherein the self-assembling peptide comprises a sequence selected from the group consisting of SEQ ID Nos: 1 to 16.

7. The immunogenic composition according to claim 1, wherein the self-assembling peptide comprises a sequence selected from the group consisting of SEQ ID Nos: 1, 15 and 16.

8. The immunogenic composition according to claim 1, wherein the self-assembling peptide comprises SEQ ID No: 1.

9. The immunogenic composition according to claim 1, wherein a molecular weight of the antigen is 6.0 kDa to $1.0 \times 10^3$ kDa.

10. The immunogenic composition according to claim 1, wherein the antigen contains a positively charged protein at a physiological pH.

11. The immunogenic composition according to claim 1, wherein the antigen comprises an antigen derived from food, a mite, house dust, a plant, or an animal.

12. The immunogenic composition according to claim 1, wherein the antigen comprises an antigen of a mite allergy, an antigen of an egg allergy, or pollen.

13. The immunogenic composition according to claim 1, wherein the antigen comprises at least one selected from a group consisting of ovalbumin, casein, lysozyme, and papain.

14. A method for producing the immunogenic composition according to claim 1, the method comprising:
(A-I) determining a combination of the antigen and the self-assembling peptide; and
(A-II) mixing an aqueous medium with the determined combination of the antigen and the self-assembling peptide.

* * * * *

SEQUENCE LISTING

```
<160> NUMBER OF SEQ ID NOS: 18

<210> SEQ ID NO 1
<211> LENGTH: 13
<212> TYPE: PRT
<213> ORGANISM: Artificial Sequence
<220> FEATURE:
<223> OTHER INFORMATION: self-assembling peptide

<400> SEQUENCE: 1

Arg Leu Asp Leu Arg Leu Ala Leu Arg Leu Asp Leu Arg
1               5                   10

<210> SEQ ID NO 2
<211> LENGTH: 13
<212> TYPE: PRT
<213> ORGANISM: Artificial Sequence
<220> FEATURE:
<223> OTHER INFORMATION: self-assembling peptide
```

```
<400> SEQUENCE: 2

Arg Leu Asp Leu Arg Leu Leu Leu Arg Leu Asp Leu Arg
1               5                   10

<210> SEQ ID NO 3
<211> LENGTH: 13
<212> TYPE: PRT
<213> ORGANISM: Artificial Sequence
<220> FEATURE:
<223> OTHER INFORMATION: self-assembling peptide

<400> SEQUENCE: 3

Arg Ala Asp Leu Arg Leu Ala Leu Arg Leu Asp Leu Arg
1               5                   10

<210> SEQ ID NO 4
<211> LENGTH: 13
<212> TYPE: PRT
<213> ORGANISM: Artificial Sequence
<220> FEATURE:
<223> OTHER INFORMATION: self-assembling peptide

<400> SEQUENCE: 4

Arg Leu Asp Leu Arg Leu Ala Leu Arg Leu Asp Ala Arg
1               5                   10

<210> SEQ ID NO 5
<211> LENGTH: 13
<212> TYPE: PRT
<213> ORGANISM: Artificial Sequence
<220> FEATURE:
<223> OTHER INFORMATION: self-assembling peptide

<400> SEQUENCE: 5

Arg Ala Asp Leu Arg Leu Leu Leu Arg Leu Asp Leu Arg
1               5                   10

<210> SEQ ID NO 6
<211> LENGTH: 13
<212> TYPE: PRT
<213> ORGANISM: Artificial Sequence
<220> FEATURE:
<223> OTHER INFORMATION: self-assembling peptide

<400> SEQUENCE: 6

Arg Ala Asp Leu Arg Leu Leu Leu Arg Leu Asp Ala Arg
1               5                   10

<210> SEQ ID NO 7
<211> LENGTH: 13
<212> TYPE: PRT
<213> ORGANISM: Artificial Sequence
<220> FEATURE:
<223> OTHER INFORMATION: self-assembling peptide

<400> SEQUENCE: 7

Arg Leu Asp Leu Arg Ala Leu Leu Arg Leu Asp Leu Arg
1               5                   10

<210> SEQ ID NO 8
<211> LENGTH: 13
<212> TYPE: PRT
<213> ORGANISM: Artificial Sequence
<220> FEATURE:
<223> OTHER INFORMATION: self-assembling peptide

<400> SEQUENCE: 8
```

```
Arg Leu Asp Leu Arg Leu Leu Ala Arg Leu Asp Leu Arg
1               5                   10

<210> SEQ ID NO 9
<211> LENGTH: 12
<212> TYPE: PRT
<213> ORGANISM: Artificial Sequence
<220> FEATURE:
<223> OTHER INFORMATION: self-assebling peptide

<400> SEQUENCE: 9

Leu Glu Leu Ser Leu Glu Leu Ser Leu Glu Leu Ser
1               5                   10

<210> SEQ ID NO 10
<211> LENGTH: 12
<212> TYPE: PRT
<213> ORGANISM: Artificial Sequence
<220> FEATURE:
<223> OTHER INFORMATION: self-assebling peptide

<400> SEQUENCE: 10

Ser Leu Asp Leu Lys Leu Asp Leu Ser Leu Asp Leu
1               5                   10

<210> SEQ ID NO 11
<211> LENGTH: 16
<212> TYPE: PRT
<213> ORGANISM: Artificial Sequence
<220> FEATURE:
<223> OTHER INFORMATION: self-assembling peptide

<400> SEQUENCE: 11

Ser Ala Glu Ala Lys Ala Glu Ala Ser Ala Glu Ala Lys Ala Glu Ala
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: self-assembling peptide

<400> SEQUENCE: 12

Ser Ala Glu Ala Ser Ala Glu Ala Ser Ala Glu Ala Lys Ala Glu Ala
1               5                   10                  15

<210> SEQ ID NO 13
<211> LENGTH: 12
<212> TYPE: PRT
<213> ORGANISM: Artificial Sequence
<220> FEATURE:
<223> OTHER INFORMATION: self-assembling peptide

<400> SEQUENCE: 13

Arg Leu Asn Leu Arg Leu Asp Leu Arg Leu Asn Leu
1               5                   10

<210> SEQ ID NO 14
<211> LENGTH: 16
<212> TYPE: PRT
<213> ORGANISM: Artificial Sequence
<220> FEATURE:
<223> OTHER INFORMATION: self-assembling peptide

<400> SEQUENCE: 14
```

Arg Ala Gln Ala Arg Ala Gln Ala Arg Ala Gln Ala Arg Ala Gln Ala
1               5                   10                  15

<210> SEQ ID NO 15
<211> LENGTH: 13
<212> TYPE: PRT
<213> ORGANISM: Artificial Sequence
<220> FEATURE:
<223> OTHER INFORMATION: self-assembling peptide

<400> SEQUENCE: 15

Arg Leu Asp Leu Arg Leu Ser Leu Arg Leu Asp Leu Arg
1               5                   10

<210> SEQ ID NO 16
<211> LENGTH: 13
<212> TYPE: PRT
<213> ORGANISM: Artificial Sequence
<220> FEATURE:
<223> OTHER INFORMATION: self-assembling peptide

<400> SEQUENCE: 16

Arg Leu Asp Leu Arg Leu Asn Leu Arg Leu Asp Leu Arg
1               5                   10

<210> SEQ ID NO 17
<211> LENGTH: 7
<212> TYPE: PRT
<213> ORGANISM: Artificial Sequence
<220> FEATURE:
<223> OTHER INFORMATION: peptide

<400> SEQUENCE: 17

Arg Leu Asp Leu Arg Leu Ala
1               5

<210> SEQ ID NO 18
<211> LENGTH: 16
<212> TYPE: PRT
<213> ORGANISM: Artificial Sequence
<220> FEATURE:
<223> OTHER INFORMATION: self-assembling peptide

<400> SEQUENCE: 18

Arg Ala Asp Ala Arg Ala Asp Ala Arg Ala Asp Ala Arg Ala Asp Ala
1               5                   10                  15